(12) United States Patent
LaVon et al.

(10) Patent No.: US 7,695,463 B2
(45) Date of Patent: Apr. 13, 2010

(54) DISPOSABLE ABSORBENT ARTICLE HAVING DUAL LAYER BARRIER CUFF STRIPS

(75) Inventors: Gary Dean LaVon, Liberty Township, OH (US); Kevin Michael Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 457 days.

(21) Appl. No.: 11/158,563

(22) Filed: Jun. 22, 2005

(65) Prior Publication Data

US 2006/0293637 A1     Dec. 28, 2006

(51) Int. Cl.
*A61F 13/15*     (2006.01)

(52) U.S. Cl. .............. 604/385.28; 604/385.29; 604/385.3; 604/385.24; 604/385.25

(58) Field of Classification Search ............ 604/385.28, 604/385.29, 385.3, 385.24, 385.25
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |

(Continued)

FOREIGN PATENT DOCUMENTS

DE     19732499     2/1999

(Continued)

OTHER PUBLICATIONS

U.S. Appl. No. 11/231,511, filed Sep. 21, 2005, LaVon et al.

(Continued)

*Primary Examiner*—Jacqueline F. Stephens
(74) *Attorney, Agent, or Firm*—Richard L. Alexander

(57) ABSTRACT

A disposable absorbent article includes two laterally opposing longitudinally extending barrier cuff strips attached to an absorbent assembly in laterally opposing attachment zones. Each barrier cuff strip includes an upper layer and a lower layer at least between its proximal edge and the attachment zones. A longitudinally extending elastic gathering member is attached to each barrier cuff strip adjacent to its proximal edge. When the article is worn, the elastic gathering members contract and raise the barrier cuff strips to form side barriers. The absorbent assembly includes an absorbent core that may contain superabsorbent particles, which may be contained inside pockets. A portion of the absorbent assembly such as the portion that lies between the barrier cuff strip attachment zones may be extensible and may include a water-impermeable layer. The laterally opposing attachment zones may act as dams preventing a lateral flow of liquid bodily waste.

6 Claims, 11 Drawing Sheets

U.S. PATENT DOCUMENTS

| | | |
|---|---|---|
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,578,155 A | 5/1971 | Small et al. |
| 3,592,194 A | 7/1971 | Duncan |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Oephel |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,578,072 A | 3/1986 | Lancaster |
| 4,578,702 A | 3/1986 | Campbell |
| 4,585,450 A | 4/1986 | Rosch et al. |
| 4,589,878 A | 5/1986 | Mitrani |
| 4,601,717 A | 7/1986 | Blevins |
| 4,610,678 A | 9/1986 | Weisman et al. |
| 4,636,207 A | 1/1987 | Buell |
| 4,670,011 A | 6/1987 | Mesek |
| 4,670,012 A | 6/1987 | Johnson |
| 4,680,030 A | 7/1987 | Coates et al. |
| 4,681,581 A | 7/1987 | Coates |
| 4,690,680 A | 9/1987 | Higgins |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,747,846 A | 5/1988 | Boland et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,032,120 A * | 7/1991 | Freeland et al. ........ 604/385.27 |
| 5,037,416 A | 8/1991 | Allen et al. |
| 5,071,414 A | 12/1991 | Elliott |
| 5,085,654 A | 2/1992 | Buell |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | Desmarais et al. |
| 5,269,775 A | 12/1993 | Freeland et al. |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,415,644 A | 5/1995 | Enloe |
| 5,476,458 A | 12/1995 | Glaug et al. |
| 5,507,895 A | 4/1996 | Suekane |
| 5,518,801 A | 5/1996 | Chappell et al. |
| 5,531,730 A | 7/1996 | Dreier |
| 5,542,943 A | 8/1996 | Sageser |
| 5,549,592 A | 8/1996 | Fries et al. |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,829 A | 12/1996 | Lavash et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |

| | | | | | | |
|---|---|---|---|---|---|---|
| 5,622,589 | A | 4/1997 | Johnson et al. | 6,423,048 B1 | 7/2002 | Suzuki et al. |
| 5,624,424 | A | 4/1997 | Saisaka et al. | 6,432,098 B1 | 8/2002 | Kline et al. |
| 5,625,222 | A | 4/1997 | Yoneda et al. | 6,432,099 B2 | 8/2002 | Rönnberg |
| 5,626,571 | A | 5/1997 | Young et al. | 6,443,933 B1 | 9/2002 | Suzuki et al. |
| 5,635,191 | A | 6/1997 | Roe et al. | 6,461,342 B2 | 10/2002 | Tanji et al. |
| 5,643,243 | A | 7/1997 | Klemp | 6,461,343 B1 | 10/2002 | Schaefer et al. |
| 5,643,588 | A | 7/1997 | Roe et al. | 6,475,201 B2 | 11/2002 | Saito et al. |
| H1674 | H | 8/1997 | Ames et al. | 6,478,786 B1 | 11/2002 | Glaug et al. |
| 5,662,638 | A | 9/1997 | Johnson et al. | 6,494,872 B1 | 12/2002 | Suzuki et al. |
| 5,674,215 | A | 10/1997 | Ronnberg | 6,494,873 B2 | 12/2002 | Karlsson et al. |
| 5,685,874 | A | 11/1997 | Buell et al. | 6,520,947 B1 | 2/2003 | Tilly et al. |
| 5,691,035 | A | 11/1997 | Chappell et al. | 6,524,294 B1 | 2/2003 | Hilston et al. |
| 5,695,488 | A | 12/1997 | Sosalla | 6,585,712 B2 | 7/2003 | Yoshimasa |
| 5,723,087 | A | 3/1998 | Chappell et al. | 6,585,713 B1 | 7/2003 | LeMahieu et al. |
| 5,733,275 | A | 3/1998 | Davis et al. | 6,605,070 B2 | 8/2003 | Ludwig et al. |
| 5,749,866 | A | 5/1998 | Roe et al. | 6,626,881 B2 | 9/2003 | Shingu et al. |
| 5,752,947 | A | 5/1998 | Awolin | 6,648,869 B1 | 11/2003 | Gillies et al. |
| 5,772,825 | A | 6/1998 | Schmitz | 6,648,870 B2 | 11/2003 | Itoh et al. |
| 5,776,121 | A | 7/1998 | Roe et al. | 6,648,871 B2 | 11/2003 | Kusibojoska et al. |
| 5,779,831 | A | 7/1998 | Schmitz | 6,652,696 B2 | 11/2003 | Kuen et al. |
| 5,797,894 | A | 8/1998 | Cadieux et al. | 6,682,515 B1 | 1/2004 | Mizutani et al. |
| 5,810,800 | A | 9/1998 | Hunter et al. | 6,689,115 B1 | 2/2004 | Popp et al. |
| 5,814,035 | A | 9/1998 | Gryskiewicz et al. | 6,726,792 B1 | 4/2004 | Johnson et al. |
| 5,820,618 | A | 10/1998 | Roberts et al. | 6,730,070 B2 | 5/2004 | Holmquist |
| 5,846,232 | A | 12/1998 | Serbiak et al. | 6,755,808 B2 | 6/2004 | Balogh et al. |
| 5,851,204 | A | 12/1998 | Mizutani | 6,818,083 B2 | 11/2004 | McAmish et al. |
| 5,858,013 | A | 1/1999 | Kling | 6,840,930 B1 | 1/2005 | Miyamoto et al. |
| 5,865,823 | A | 2/1999 | Curro | 6,880,211 B2 | 4/2005 | Jackson et al. |
| 5,873,868 | A | 2/1999 | Nakahata | 6,923,797 B2 | 8/2005 | Shinohara et al. |
| 5,876,391 | A | 3/1999 | Roe et al. | 6,962,578 B1 | 11/2005 | LaVon |
| 5,891,544 | A | 4/1999 | Chappell et al. | 6,972,010 B2 | 12/2005 | Pesce et al. |
| 5,897,545 | A | 4/1999 | Kline et al. | 7,013,941 B2 | 3/2006 | Schneider et al. |
| 5,904,673 | A | 5/1999 | Roe et al. | 7,014,632 B2 | 3/2006 | Takino et al. |
| 5,931,825 | A | 8/1999 | Kuen et al. | 7,037,299 B2 | 5/2006 | Turi et al. |
| 5,947,949 | A | 9/1999 | Inoue et al. | 7,048,726 B2 | 5/2006 | Kusagawa et al. |
| 5,951,536 | A | 9/1999 | Osborn, III et al. | 7,066,921 B2 | 6/2006 | Schmoker et al. |
| 5,957,908 | A | 9/1999 | Kline et al. | D525,706 S | 7/2006 | Pargass |
| 5,968,029 | A | 10/1999 | Chappell et al. | 7,094,227 B2 | 8/2006 | Ishiguro et al. |
| 5,997,521 | A | 12/1999 | Robles et al. | 7,112,193 B2 | 9/2006 | Otsubo |
| 6,004,306 | A | 12/1999 | Robles et al. | 7,160,281 B2 | 1/2007 | Leminh et al. |
| 6,022,430 | A | 2/2000 | Blenke et al. | 7,195,622 B2 | 3/2007 | Lindstrom |
| 6,022,431 | A | 2/2000 | Blenke et al. | 7,291,137 B2 | 11/2007 | LaVon et al. |
| 6,042,673 | A | 3/2000 | Johnson et al. | 7,320,684 B2 | 1/2008 | LaVon et al. |
| 6,102,892 | A | 8/2000 | Putzer et al. | 7,347,848 B2 | 3/2008 | Fernfors |
| 6,107,537 | A | 8/2000 | Elder et al. | 7,435,244 B2 | 10/2008 | Schroer, Jr. et al. |
| 6,110,157 | A | 8/2000 | Schmidt | 7,462,172 B2 | 12/2008 | Wright et al. |
| 6,117,121 | A | 9/2000 | Faulks et al. | 2002/0045881 A1 | 4/2002 | Kusibojoska et al. |
| 6,117,803 | A | 9/2000 | Morman et al. | 2002/0087139 A1 | 7/2002 | Popp et al. |
| 6,120,486 | A | 9/2000 | Toyoda et al. | 2002/0151858 A1 | 10/2002 | Karami et al. |
| 6,120,487 | A | 9/2000 | Ashton | 2002/0151861 A1 | 10/2002 | Klemp et al. |
| 6,120,489 | A | 9/2000 | Johnson et al. | 2002/0173767 A1 | 11/2002 | Popp et al. |
| 6,120,866 | A | 9/2000 | Arakawa et al. | 2003/0003269 A1 | 1/2003 | Lee et al. |
| 6,129,720 | A | 10/2000 | Blenke et al. | 2003/0023220 A1 | 1/2003 | Ukegawa et al. |
| 6,156,424 | A | 12/2000 | Taylor | 2003/0088223 A1 | 5/2003 | Vogt et al. |
| 6,165,160 | A | 12/2000 | Suzuki et al. | 2003/0105447 A1 | 6/2003 | Widlund et al. |
| 6,174,302 | B1 | 1/2001 | Kumasaka | 2003/0144644 A1 | 7/2003 | Murai et al. |
| 6,177,607 | B1 | 1/2001 | Blaney et al. | 2003/0148694 A1 | 8/2003 | Ghiam |
| 6,186,996 | B1 | 2/2001 | Martin | 2003/0233082 A1 | 12/2003 | Kline et al. |
| 6,210,386 | B1 | 4/2001 | Inoue | 2004/0022998 A1 | 2/2004 | Miyamoto et al. |
| 6,210,390 | B1 | 4/2001 | Karlsson | 2004/0082928 A1 | 4/2004 | Pesce et al. |
| 6,238,380 | B1 | 5/2001 | Sasaki | 2004/0122404 A1 | 6/2004 | Meyer et al. |
| 6,241,716 | B1 | 6/2001 | Rönnberg | 2004/0122411 A1 | 6/2004 | Hancock-Cooke |
| 6,306,122 | B1 | 10/2001 | Narawa et al. | 2004/0127868 A1 | 7/2004 | Olson et al. |
| 6,322,552 | B1 | 11/2001 | Blenke et al. | 2004/0127890 A1 | 7/2004 | Bacher |
| 6,325,787 | B1 | 12/2001 | Roe et al. | 2004/0147890 A1 | 7/2004 | Nakahata et al. |
| 6,334,858 | B1 | 1/2002 | Rönnberg et al. | 2004/0162536 A1 | 8/2004 | Becker et al. |
| 6,350,332 | B1 | 2/2002 | Thomas et al. | 2004/0167486 A1 | 8/2004 | Busam et al. |
| 6,364,863 | B1 | 4/2002 | Yamamoto et al. | 2004/0193133 A1 | 9/2004 | Desai et al. |
| 6,402,729 | B1 | 6/2002 | Boberg et al. | 2004/0225271 A1 | 11/2004 | Datta et al. |
| 6,402,731 | B1 | 6/2002 | Suprise et al. | 2004/0236299 A1 | 11/2004 | Tsang et al. |
| 6,410,820 | B1 | 6/2002 | McFall et al. | 2004/0249355 A1 | 12/2004 | Tanio et al. |
| 6,413,249 | B1 | 7/2002 | Turi et al. | 2005/0004543 A1 | 1/2005 | Schroer et al. |
| 6,419,667 | B1 | 7/2002 | Avalon et al. | 2005/0004548 A1 | 1/2005 | Otsubo et al. |

| | | |
|---|---|---|
| 2005/0038401 A1 | 2/2005 | Suzuki et al. |
| 2005/0085784 A1 | 4/2005 | LeMinh et al. |
| 2005/0171499 A1 | 8/2005 | Nigam et al. |
| 2005/0203475 A1 | 9/2005 | LaVon et al. |
| 2005/0203479 A1 | 9/2005 | Sakaguchi et al. |
| 2005/0288645 A1 | 12/2005 | LaVon |
| 2005/0288646 A1 | 12/2005 | LaVon |
| 2006/0264860 A1 | 11/2006 | Beck et al. |
| 2006/0264861 A1 | 11/2006 | LaVon et al. |
| 2006/0271010 A1 | 11/2006 | LaVon |
| 2006/0293638 A1 | 12/2006 | LaVon et al. |
| 2007/0032770 A1 | 2/2007 | LaVon et al. |
| 2007/0049897 A1 | 3/2007 | LaVon et al. |
| 2007/0066951 A1 | 3/2007 | LaVon et al. |
| 2007/0066952 A1 | 3/2007 | LaVon et al. |
| 2007/0066953 A1 | 3/2007 | LaVon et al. |
| 2007/0118088 A1 | 5/2007 | LaVon |
| 2007/0173780 A1 | 7/2007 | LaVon et al. |
| 2007/0173782 A1 | 7/2007 | LaVon |
| 2008/0183149 A1 | 7/2008 | LaVon et al. |
| 2008/0208155 A1 | 8/2008 | LaVon et al. |
| 2008/0208156 A1 | 8/2008 | LaVon et al. |
| 2008/0234649 A1 | 9/2008 | Hamall et al. |

FOREIGN PATENT DOCUMENTS

| | | |
|---|---|---|
| EP | 0 206 208 | 12/1986 |
| EP | 0 206 208 A1 | 12/1986 |
| EP | 374542 | 6/1990 |
| EP | 0 403 832 B1 | 12/1990 |
| EP | 0403832 | 12/1990 |
| EP | 0 761 194 A2 | 3/1997 |
| EP | 0 893 115 A2 | 1/1999 |
| EP | 0 916 327 B1 | 5/1999 |
| EP | 0 951 890 A2 | 10/1999 |
| EP | 0 793 469 B9 | 6/2002 |
| EP | 1 224 922 A2 | 7/2002 |
| EP | 1 447 066 A1 | 8/2004 |
| EP | 1 447 067 A1 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 | 12/2001 |
| FR | 2 810 234 A1 | 12/2001 |
| GB | 1 307 441 | 2/1973 |
| GB | 1 513 055 | 6/1978 |
| GB | 2 101 468 | 1/1983 |
| GB | 2 101 468 A | 1/1983 |
| GB | 2 262 873 A | 7/1993 |
| JP | 04 122256 | 4/1992 |
| JP | 04 122256 A | 4/1992 |
| JP | 11318980 | 11/1999 |
| WO | WO 95/16746 | 6/1995 |
| WO | WO 95/19753 | 7/1995 |
| WO | WO 95/29657 | 11/1995 |
| WO | WO 95/29657 A1 | 11/1995 |
| WO | WO 98/16179 A1 | 4/1998 |
| WO | WO 99/13813 A1 | 3/1999 |
| WO | WO 03/009794 A3 | 2/2003 |
| WO | WO 2004/105664 | 12/2004 |
| WO | WO 2005/016211 | 2/2005 |
| WO | WO 2005/081937 | 9/2005 |
| WO | WO 2005/087164 A1 | 9/2005 |
| WO | WO 2007/000315 | 1/2007 |
| WO | WO 2007/000315 A1 | 1/2007 |

OTHER PUBLICATIONS

U.S. Appl. No. 11/231,512, filed Sep. 21, 2005, LaVon et al.
U.S. Appl. No. 11/231,500, filed Sep. 21, 2005, LaVon et al.
U.S. Appl. No. 11/232,193, filed Sep. 21, 2005, LaVon et al.
U.S. Appl. No. 11/286,612, filed Nov. 23, 2005, LaVon.
International Search Report, dated Nov. 28, 2006.
U.S. Appl. No. 10/880,128, filed Jun. 29, 2004, Office Action dated Jun. 30, 2009.
U.S. Appl. No. 10/880,128, filed Jun. 29, 2004, Office Action dated Dec. 4, 2008.
U.S. Appl. No. 10/880,128, filed Jun. 29, 2004, Office Action dated Jun. 12, 2008.
U.S. Appl. No. 10/880,128, filed Jun. 29, 2004, Office Action dated Dec. 10, 2007.
U.S. Appl. No. 10/880,128, filed Jun. 29, 2004, Office Action dated Jun. 22, 2007.
U.S. Appl. No. 10/880,128, filed Jun. 29, 2004, Office Action dated Jan. 26, 2007.
U.S. Appl. No. 10/880,128, filed Jun. 29, 2004, Office Action dated Aug. 9, 2006.
U.S. Appl. No. 11/133,818, filed May 20, 2005, Office Action dated Apr. 1, 2009.
U.S. Appl. No. 11/133,818, filed May 20, 2005, Office Action dated Dec. 9, 2008.
U.S. Appl. No. 11/133,818, filed May 20, 2005, Office Action dated Jun. 18, 2008.
U.S. Appl. No. 11/133,818, filed May 20, 2005, Office Action dated Dec. 31, 2007.
U.S. Appl. No. 11/133,818, filed May 20, 2005, Office Action dated Jun. 26, 2007.
U.S. Appl. No. 11/159,916, filed Jun. 23, 2005, Notice of Allowance dated Sep. 17, 2009.
U.S. Appl. No. 11/159,916, filed Jun. 23, 2005, Notice of Allowance dated Oct. 17, 2008.
U.S. Appl. No. 11/159,916, filed Jun. 23, 2005, Office Action dated Apr. 18, 2008.
U.S. Appl. No. 11/159,916, filed Jun. 23, 2005, Office Action dated Nov. 1, 2007.
U.S. Appl. No. 11/231,511, filed Sep. 21, 2005, Office Action dated Jun. 19, 2009.
U.S. Appl. No. 11/231,511, filed Sep. 21, 2005, Office Action dated Dec. 30, 2008.
U.S. Appl. No. 11/231,511, filed Sep. 21, 2005, Office Action dated Sep. 23, 2008.
U.S. Appl. No. 11/231,511, filed Sep. 21, 2005, Office Action dated Mar. 4, 2008.
U.S. Appl. No. 11/231,511, filed Sep. 21, 2005, Office Action dated Aug. 22, 2007.
U.S. Appl. No. 11/231,511, filed Sep. 21, 2005, Office Action dated Jun. 7, 2006.
U.S. Appl. No. 11/231,512, filed Sep. 21, 2005, Office Action dated Jul. 22, 2009.
U.S. Appl. No. 11/231,512, filed Sep. 21, 2005, Office Action dated Jan. 6, 2009.
U.S. Appl. No. 11/231,512, filed Sep. 21, 2005, Office Action dated Jun. 27, 2008.
U.S. Appl. No. 11/231,500, filed Sep. 21, 2005, Office Action dated Jun. 24, 2009.
U.S. Appl. No. 11/231,500, filed Sep. 21, 2005, Office Action dated Jan. 8, 2009.
U.S. Appl. No. 11/231,500, filed Sep. 21, 2005, Office Action dated Sep. 22, 2008.
U.S. Appl. No. 11/231,500, filed Sep. 21, 2005, Office Action dated Mar. 4, 2008.
U.S. Appl. No. 11/231,500, filed Sep. 21, 2005, Office Action dated Aug. 22, 2007.
U.S. Appl. No. 11/286,612, filed Nov. 23, 2005, Office Action dated Jul. 23, 2009.
U.S. Appl. No. 11/286,612, filed Nov. 23, 2005, Office Action dated Dec. 24, 2008.

* cited by examiner

DISPOSABLE ABSORBENT ARTICLE HAVING DUAL LAYER BARRIER CUFF STRIPS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

The present invention provides a disposable absorbent article including two laterally opposing longitudinally extending dual layer barrier cuff strips attached to an absorbent assembly in laterally opposing attachment zones. Each barrier cuff strip is water vapor-permeable and includes a water-impermeable layer and may be extensible. A longitudinally extending elastic gathering member is attached to each barrier cuff strip adjacent to its proximal edge. When the article is worn, the elastic gathering members contract and raise the barrier cuff strips to form breathable side barriers. The absorbent assembly includes an absorbent core that may contain superabsorbent particles, which may be contained inside pockets. A portion of the absorbent assembly such as the portion that lies between the barrier cuff strip attachment zones may be extensible and may include a water-impermeable layer. The laterally opposing attachment zones may act as dams preventing a lateral flow of liquid bodily waste.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In the drawing figures and in the written description, lowercase letters appended to reference numerals indicate generally symmetric elements, e.g., the left and right side edges of the absorbent assembly 200 are respectively identified by the reference numerals 237a and 237b. A reference numeral without an appended lowercase letter identifies all of the elements to which that particular reference numeral applies.

DETAILED DESCRIPTION OF THE INVENTION

Figure 1:
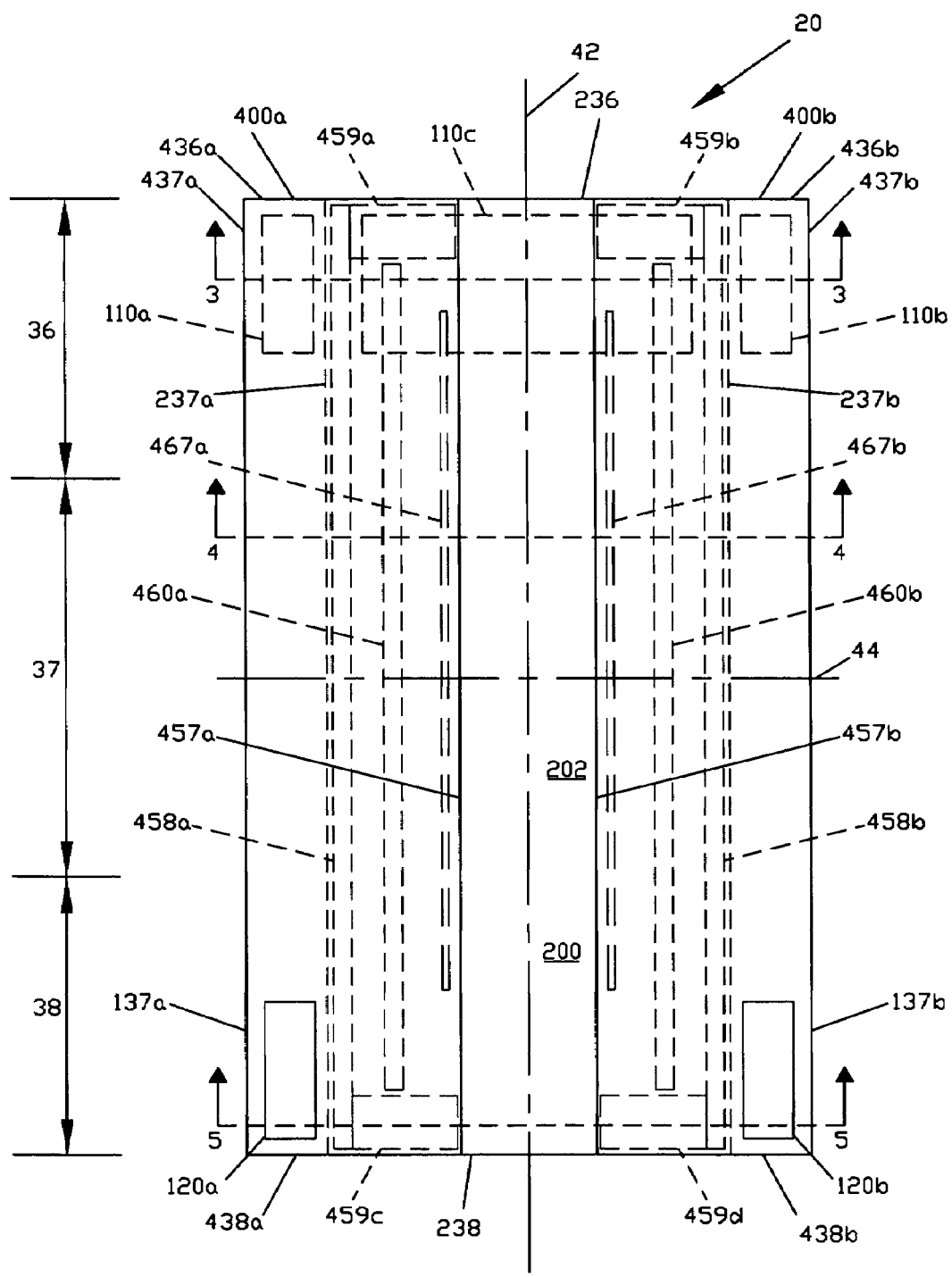
FIG. 1 is a plan view of an exemplary diaper 20, shown in its flat, uncontracted state, i.e., without the contraction induced by elastic members, and with the interior portion of the diaper 20 that faces inwardly toward the wearer and contacts the wearer facing the viewer.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within 45° of the longitudinal direction are considered to be "longitudinal".

The term "lateral" refers to a direction running from a side edge to an opposing side edge of the article and generally at a right angle to the longitudinal direction. Directions within 45° of the lateral direction are considered to be "lateral".

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that, once set, sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

Description of Exemplary Diaper Embodiments

Reference is made to FIG. 1, FIG. 2, FIG. 3, FIG. 4, FIG. 5, FIG. 6, FIG. 7, and FIG. 8 for this section of this description.

One end portion of the exemplary diaper 20 is configured as a front waist region 36, the longitudinally opposing end portion is configured as a back waist region 38, and an intermediate portion is configured as a crotch region 37.

The basic structure of the diaper 20 includes an absorbent assembly 200, which has a front edge 236, a back edge 238, a left side edge 237a, a right side edge 237b, an interior surface 202, and an exterior surface 204. A longitudinal axis 42 extends through the midpoints of the front edge 236 and the back edge 238 and a lateral axis 44 extends through the midpoints of the side edges 237.

The basic structure of the diaper 20 also includes two laterally opposing longitudinally extending barrier cuff strips designated the left barrier cuff strip 400a and the right barrier cuff strip 400b. The barrier cuff strips have respective front waist edges 436, back waist edges 438, proximal edges 457, and distal edges 437. The barrier cuff strip distal edges 437 form the respective side edges 137 of the diaper 20.

The barrier cuff strips 400 and the absorbent assembly 200 are attached together in laterally opposing longitudinally extending attachment zones such as the exemplary attachment zones 420 shown in FIG. 2, FIG. 3, FIG. 4, and FIG. 5.

When the diaper 20 is worn on the lower torso of a wearer, the front waist edges 436 of the barrier cuff strips, the front edge 236 of the absorbent assembly, the back waist edges 438 of the barrier cuff strips, and the back edge 238 of the absorbent assembly encircle the waist of the wearer, the side edges 137 of the diaper encircle the legs of the wearer, the crotch region 37 is generally positioned between the legs of the wearer, and the absorbent assembly 200 extends from the front waist region 36 through the crotch region 37 to the back waist region 38.

A portion or the whole of each of the barrier cuff strips may be formed of an elastically extensible material or materials. Alternatively or in addition, a portion or the whole of each of the barrier cuff strips may be made extensible to a degree greater than the inherent extensibility of the material or materials from which the barrier cuff strip is made. Similarly, a portion or the whole of the absorbent assembly may be formed of an elastically extensible material or materials. Alternatively or in addition, a portion or the whole of the absorbent assembly may be made extensible to a degree greater than the inherent extensibility of the material or materials from which the absorbent assembly is made. The additional extensibility may be desirable in order to allow the diaper 20 to conform to the body of a wearer during movement by the wearer. Additional lateral extensibility may be particularly desirable to allow the user of a diaper to extend the front waist region and/or the back waist region to encircle the waist of a wearer, i.e., to tailor the waist size and fit of a diaper to the individual wearer. Such a lateral extension of the waist region or regions may give the diaper a generally hourglass shape and may impart a tailored appearance to the diaper when it is worn. In addition, the additional extensibility may be desirable in order to minimize the cost of the diaper, because a relatively lesser amount of material is needed when the material is made extensible as described.

For the purpose of fitting to the waist of the wearer, in some embodiments additional lateral extensibility in the absorbent assembly 200 is provided only between the laterally opposing attachment zones 420 where the absorbent assembly 200 and the barrier cuff strips 400 are attached together, rather than in the entire absorbent assembly.

Figure 9:
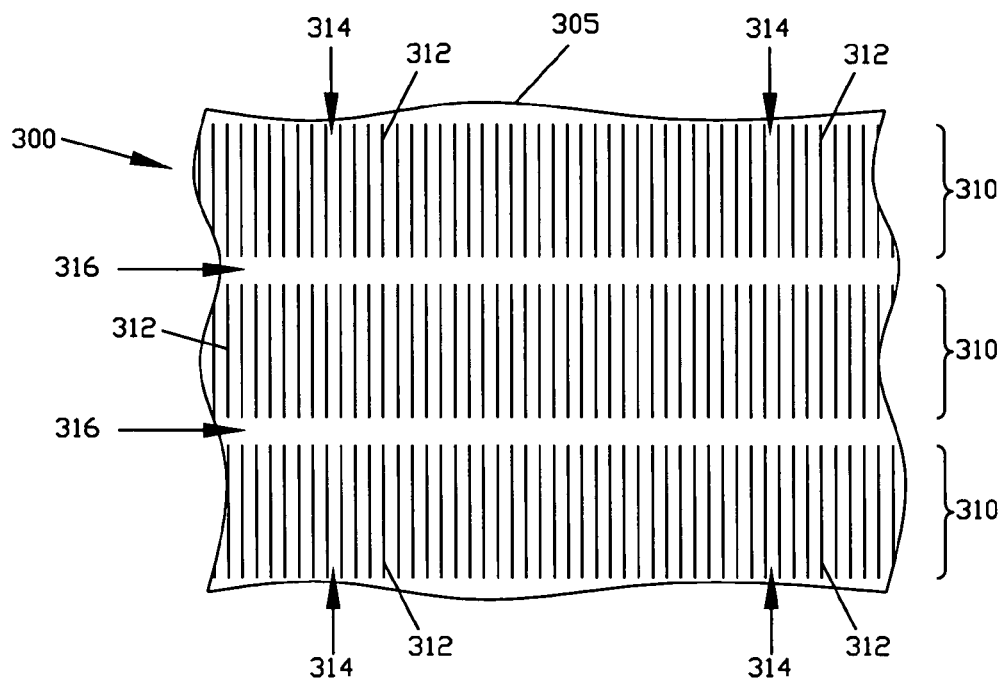
FIG. 9 is a plan view of an exemplary fragment of a formed web material.

Additional extensibility in the barrier cuff strips and/or the absorbent assembly may be provided in a variety of ways. For example, a material or materials from which the barrier cuff strips and/or the absorbent assembly is/are made may be pleated by any of many known methods. Alternatively, all or a portion of the barrier cuff strips and/or the absorbent assembly may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 9. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

Such a formed web material 305 can be laterally extended beyond its original dimension with the application of relatively less force than that required to extend the same material to the same extent when undeformed. In particular, the application of opposing divergent forces directed generally perpendicular to the ridges 312 and valleys 314 extends such a formed web material along an axis between the opposing forces and generates a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful in absorbent articles, but may be made of relatively less expensive materials that are not inherently elastic and, thus, their use may provide an advantage in terms of the cost of manufacturing the absorbent articles.

In addition, different portions of the barrier cuff strips and/or the absorbent assembly may be formed to have different ranges of extensibility and/or to be extensible to a greater or lesser degree when subjected to a given level of opposing tensile forces, i.e., to be relatively more easily or less easily extensible. Such differential extensibility may be desirable so that, for example, one or both of the waist regions may be laterally extended relatively further or relatively more easily than the crotch region.

Description of the Barrier Cuff Strips

The diaper 20 includes two laterally opposing longitudinally extending barrier cuff strips designated the left barrier cuff strip 400a and the right barrier cuff strip 400b as shown in FIG. 1, FIG. 2, FIG. 3, FIG. 4, and FIG. 5. Each barrier cuff strip includes two layers, namely an upper layer 410 and a lower layer 411, at least between its proximal edge 457 and the attachment zones 420 where the barrier cuff strips 400 and the absorbent assembly 200 are attached together. Laterally outward of the attachment zone 420, each barrier cuff strip 400 may include only one of these two layers or, alternatively, may include both of these layers, to equal or unequal lateral extents. For example, in the exemplary embodiment shown in FIG. 3, FIG. 4, and FIG. 5, the lower layer 411 of each barrier cuff strip 400 extends less far laterally outward than the upper layer 410 of the same barrier cuff strip, i.e., the distal edge 413 of the upper layer 410 lies laterally distally relative to the distal edge 414 of the lower layer 411. Alternatively, the lower layer 411 of each barrier cuff strip 400 may extend further laterally outward than the upper layer 410 of the same barrier cuff strip, i.e., the distal edge 414 of the lower layer 411 may lie laterally distally relative to the distal edge 413 of the upper layer 410. Whichever distal edge 413 or 414 of each barrier cuff strip 400 lies laterally most distally forms the distal edge 437 of that barrier cuff strip. In embodiments in which the distal edges 413 and 414 are collinear, they jointly form the distal edge 437.

The barrier cuff strips are formed of a water vapor-permeable, i.e., breathable, nonwoven material, for example a synthetic nonwoven such as spunbonded or carded polyethylene, polypropylene, polyester, or rayon. The nonwoven material preferably is hydrophobic and the dual layer nonwoven barrier cuff strip preferably is water-impermeable. Suitable hydrophobic nonwovens include SM (spunbond meltblown), SMS (spunbond meltblown spunbond), and SMMS (spunbond meltblown spunbond) composites. The materials of the water vapor-permeable barrier cuff strips 400 may be selected to balance overall product economics and function. For example, in comparison to the nonwoven materials commonly used in disposable diapers, a relatively inexpensive nonwoven having a relatively low basis weight may provide the requisite level of water-impermeability when it is doubled to form the dual layer barrier cuff strip.

Figure 12:
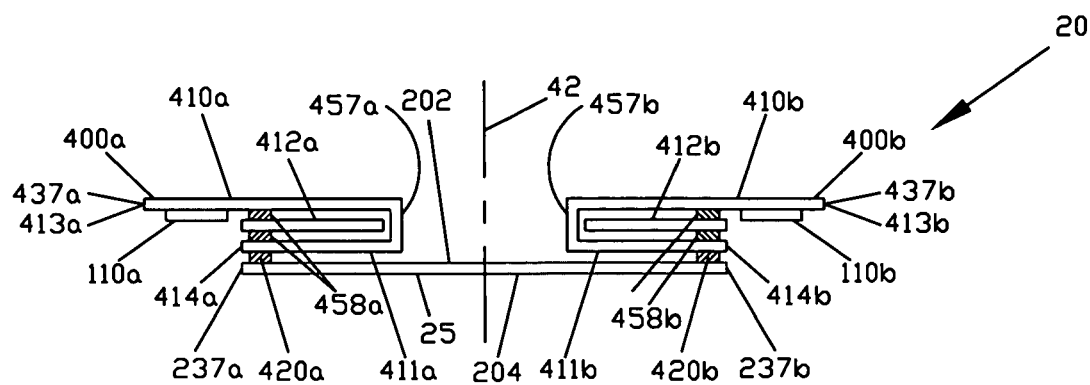
FIG. 12 is a section view of an exemplary diaper 20 taken at a section line corresponding to section line 3-3 of FIG. 1, having an additional layer 412 in the barrier cuff strip 400.

In addition to the doubled nonwoven material, each barrier cuff strip may include a third layer that is formed of a suitable water-impermeable material, for example a film of polyethylene or another polyolefin, a microporous breathable film, a hydrophobic nonwoven, or a film formed of coextruded polyolefin layers. For example, a suitable coextruded film is available from Clopay Plastic Products Co. of Mason, Ohio, U.S.A. under the designation of M18-327. Such a multi-layer barrier cuff strip may be arranged with the additional water-impermeable layer sandwiched between the nonwoven layers that provide the feel and appearance of a cloth-like outermost layer or with the additional water-impermeable layer disposed either above or below the doubled nonwoven layers. For example, FIG. 12 shows an exemplary arrangement in which an additional water-impermeable layer 412 is sandwiched between the nonwoven layers 410 and 411. Such a third layer may extend to approximately the same lateral extent as the nonwoven layer that extends least far laterally. For example, the third layer 412 in FIG. 12 extends to approximately the same lateral extent as the lower layer 411. Alternatively, such a third layer may extend to approximately the same lateral extent as the nonwoven layer that extends farthest laterally, or to an intermediate lateral extent.

The barrier cuff strips may overlap the absorbent core 250, i.e., the proximal edges 457 of the barrier cuff strips may lie laterally inward of the respective side edges 257 of the absorbent core 250. Alternatively, the barrier cuff strips may not overlap the absorbent core. The barrier cuff strips are water vapor-permeable, i.e., breathable, at least in the crotch region 37 where they form side barriers when the diaper is worn, as described in detail below.

Each of the barrier cuff strips 400 is attached to the interior surface 202 of the absorbent assembly 200 in attachment zones located at or adjacent to the front edge 236 and the back edge 238. For example, in the diaper 20 shown in FIG. 1, the barrier cuff strips 400 are attached to the interior surface 202 of the absorbent assembly 200 in the front edge and back edge attachment zones 451. These attachment zones may have equal areas or may be unequal in area.

Between the front edge and back edge attachment zones, the proximal edges 457 of the barrier cuff strips 400 remain free, i.e., are not attached to the interior surface 202 of the absorbent assembly 200. Also between the attachment zones, each barrier cuff strip preferably includes a longitudinally extensible cuff elastic member that is attached adjacent to the proximal edge of the barrier cuff strip. For example, in the exemplary diaper 20 shown in FIG. 1, elastic strands 467 are sandwiched between the upper layer 410 and the lower layer 411 and attached adjacent to the respective proximal edges 457 of the barrier cuff strips. Alternatively, each cuff elastic member may be attached on an exposed surface of the barrier cuff strip and remain exposed.

Figure 15:
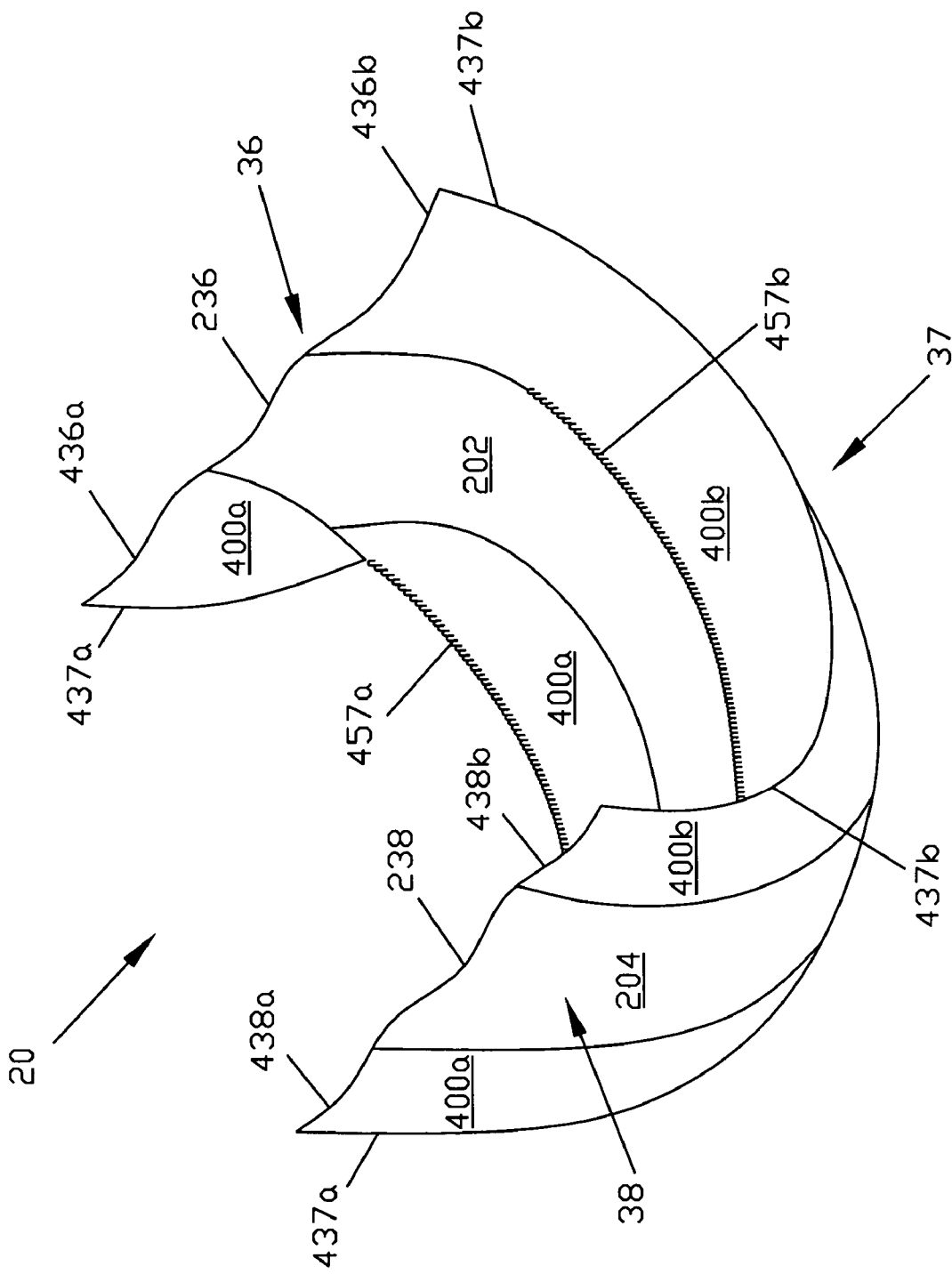
FIG. 15 is a perspective view of an exemplary diaper 20, shown in its relaxed, contracted state, i.e., with the contraction induced by elastic members, and with the interior portion of the diaper 20 that faces inwardly toward the wearer and contacts the wearer facing upward.

When stretched, the cuff elastic members allow the proximal edges of the barrier cuff strips to extend to the flat uncontracted length of the absorbent assembly, as shown in FIG. 1. When allowed to relax, the cuff elastic members contract to gather the portions of the proximal edges 457 along which the cuff elastic members are attached. For example, when the exemplary diaper 20 is in a relaxed condition, as shown in FIG. 15, the elastic strands 467 contract to gather the proximal edges 457 of the barrier cuff strips 400. The contractive forces of the elastic strands pull the front waist region 36 and the back waist region 38 toward each other and thereby bend the absorbent assembly 200 and the entire diaper 20 into a "U" shape in which the interior of the "U" shape is formed by the interior portions of the diaper. Because the proximal edges 457 remain free between the attachment zones, the contractive forces of the elastic strands lift the proximal edges 457 of the barrier cuff strips 400 away from the interior surface 202 of the absorbent assembly and thereby raise the barrier cuff strips into position to serve as side barriers. The lateral spacing of the lifted proximal edges 457 is selected to allow the deposit of bodily wastes from the lower torso of the wearer into the space between the raised barrier cuff strips. The width of each of the barrier cuff strips 400 preferably is selected to allow the lifted proximal edges 457 to fit into the leg creases of the body of the wearer to form seals to help prevent the leakage of deposited bodily waste out of the diaper.

Figure 3:
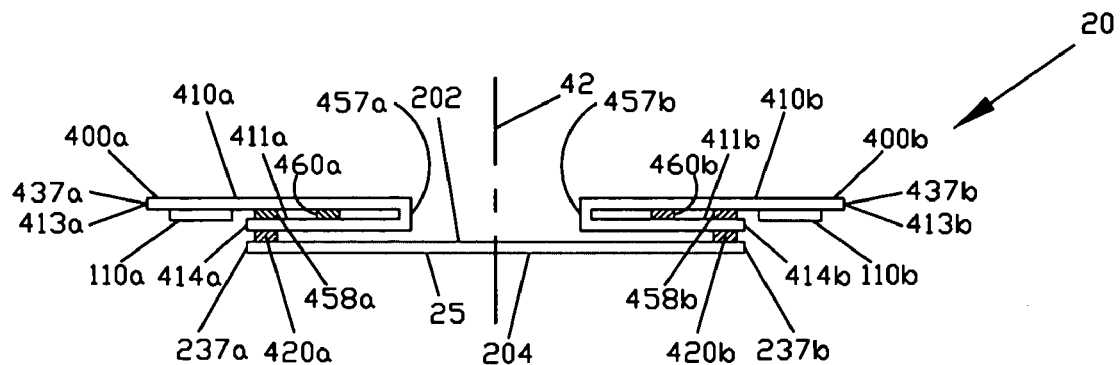
FIG. 3, FIG. 4, and FIG. 5 are section views of the diaper 20 of FIG. 1 and FIG. 2 taken at the respective section lines 3-3, 4-4, and 5-5, with the interior portion of the diaper 20 that faces inwardly toward the wearer and contacts the wearer shown facing upward.
Figure 4:
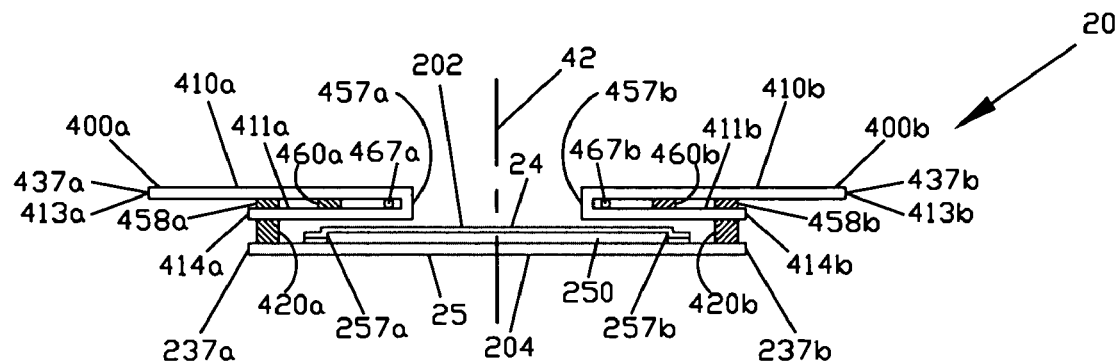
Figure 5:
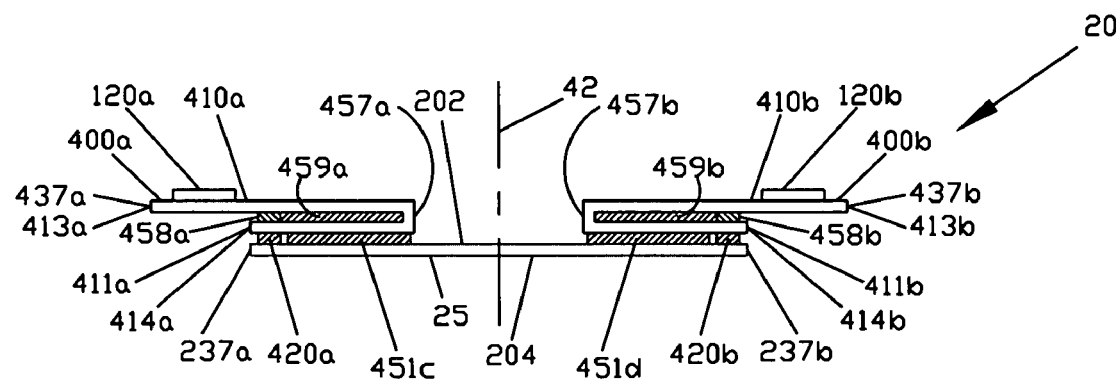
Figure 6:
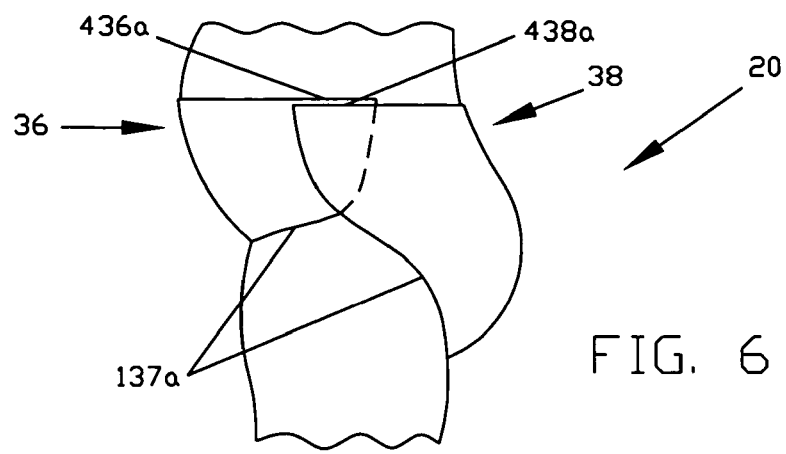
FIG. 6, FIG. 7, and FIG. 8 are simplified side, front, and back elevation views of an exemplary diaper 20 being worn about a lower torso of a wearer.
Figure 7:
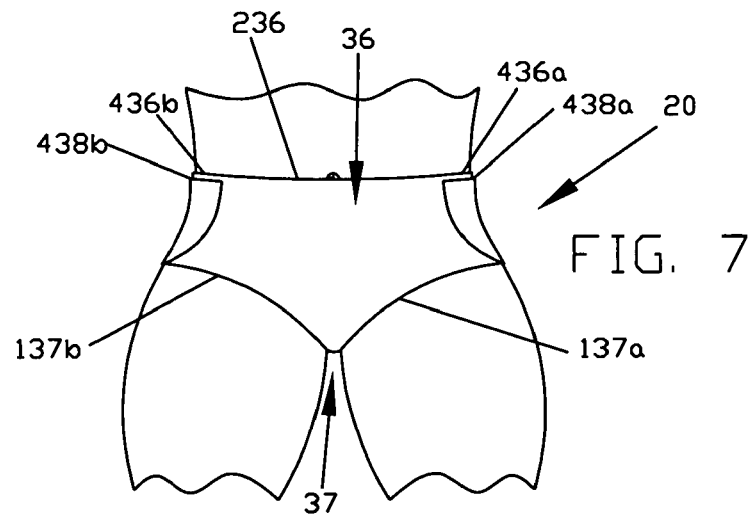
Figure 8:
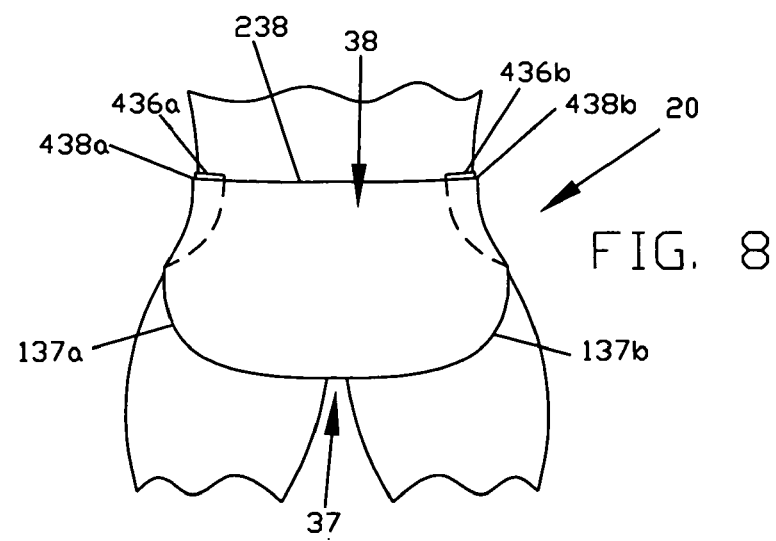

Each barrier cuff strip 400 may be doubled either by folding the barrier cuff strip or by adding a second layer to the cuff strip. For example, as shown in FIG. 3, FIG. 4, and FIG. 5, each barrier cuff strip is folded to form the two layers 410 and 411. As is also shown in these figures, the cuff elastic member may be sandwiched between the folded layers. In this embodiment, the proximal edge 457 of each barrier cuff strip 400 is formed where the barrier cuff strip is folded for doubling.

The lower layer 411 of each doubled barrier cuff strip 400 is attached to the absorbent assembly 200 in the attachment zone 420 adjacent to the respective side edge 237 of the absorbent assembly. The upper layer 410 is in turn attached to the lower layer 411 in an attachment zone 458 disposed either laterally coincidently with the attachment zone 420 or laterally further outward than the attachment zone 420. For example, the attachment zone 458 is disposed laterally coincidently with the attachment zone 420 in the exemplary diaper shown in FIG. 3, FIG. 4, and FIG. 5. When a third layer 412 is present and extends laterally outwardly to or beyond the attachment zone 420 where the lower layer 411 is attached to the absorbent assembly 200, the upper layer 410 may be attached to the third layer 412 which may in turn be attached to the lower layer 411, as shown in FIG. 12.

Figure 13:
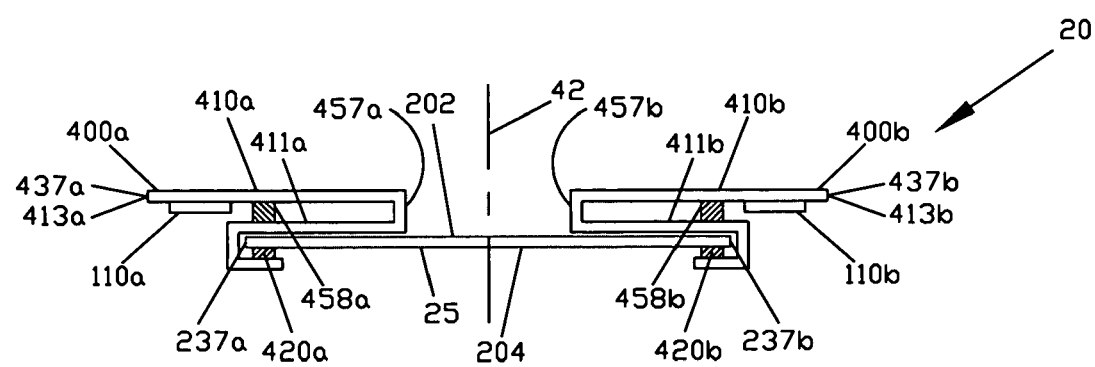
FIG. 13 is a section view of an exemplary diaper 20 taken at a section line corresponding to section line 3-3 of FIG. 1, in which the lower layer 411 of the barrier cuff strip 400 is attached to the exterior surface 204 of the absorbent assembly 200.

The lower layer 411 may be attached to the interior surface 202 of the absorbent assembly as shown in FIG. 3, FIG. 4, and FIG. 5. Alternatively, the lower layer 411 may be attached to the exterior surface 204 of the absorbent assembly. For example, in FIG. 13, the lower layer 411 of each barrier cuff strip 400 is shown wrapped over the respective side edge 237 and attached to the exterior surface 204 of the absorbent assembly 200. As another alternative, the lower layer 411 may be attached to both the interior surface 202 and the exterior surface 204.

Between the proximal edge 457 and the attachment zone 458, the layers of each doubled barrier cuff strip 400 may remain unattached to each other and thus free to contact each or separate from each other. Alternatively, the layers of each barrier cuff strip 400 may be attached together continuously or intermittently in one or more additional attachment zones located between its proximal edge 457 and the attachment zone 458 and spaced laterally inward from the attachment zone 458. These additional attachment zones extend at least in the crotch region 37 and may extend into one or both of the waist regions 36 and 38. For example, in the exemplary embodiment shown in FIG. 1, FIG. 3, and FIG. 5, the layers are attached together in laterally spaced additional attachment zones 460 extending longitudinally through the crotch region 37 and into the waist regions 36 and 38. Such additional attachment together prevents the layers from separating and thereby presenting an undesirable baggy or blousy appearance around the legs of the wearer, as well as tending to stiffen the doubled barrier cuff strips 400 slightly and thereby helping to ensure their proper fit against the body. The layers of each doubled barrier cuff strip may be attached together by adhesives, mechanical bonds, or thermal bonds, or by a combination of known bonding methods.

Alternatively, or in addition, the layers of the each doubled barrier cuff strip 400 may be attached together in the waist regions 36 and 38 adjacent to the waist edges 436 and 438, for example in laterally extending attachment zones 459 as shown in FIG. 1 and FIG. 5. This lateral attachment may be laterally intermittent or laterally continuous. When such a laterally extending attachment zone is laterally continuous from the proximal edge 457 to the attachment zone 458 where the upper layer 410 is attached to the lower layer 411, as in FIG. 1 and FIG. 5, it prevents the layers from separating and thereby presenting an undesirable unfinished appearance at the waist edges, as well as preventing the leakage at the waist edge of any liquid waste from between the layers.

An additional elastic member may be attached to each barrier cuff strip 400 laterally outward of the attachment zone 458 where the upper layer 410 and the lower layer 411 are attached together, for example, adjacent to its distal edge 437, to form an outer leg gather (not shown). Such an additional elastic member may be enclosed inside a hem formed by folding one or both of the upper layer and the lower layer of the barrier cuff strip, or may be sandwiched between the upper layer and the lower layer.

The front waist region and the back waist region can be fastened together to encircle the waist and the legs of the wearer in many ways. For example, separate fastening devices such as safety pins, separate tapes, a separate tie strap or straps, and/or a separate belt can be used for this purpose. Alternatively or in addition, fastening elements can be incorporated into the disposable absorbent article to enable a user to apply the diaper to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. Some suitable mechanical fasteners may be adapted to engage with a nonwoven layer of a diaper. For example, a mechanical fastener may engage with a nonwoven layer of a barrier cuff strip.

The fastening of the front waist region and the back waist region together may be openable and refastenable to allow for the adjustment of the fit of the diaper on the wearer and for the inspection of the interior of the diaper without fully removing it from the wearer. Alternatively, the fastening may be permanent, i.e., its opening may require the destruction of a portion of the diaper, e.g., the tearing of a portion of the diaper or the breaking of fused side seams.

Cohesive fastening patches may be formed by the application of a cohesive material onto a substrate. The cohesive material may be applied in any of a variety of patterns, such as a continuous film, discrete dots, stripes, polygons, etc., and/or spaced and interconnected geometric elements describing a grid. Suitable synthetic cohesive products are available from Andover Coated Products, Incorporated, of Salisbury, Mass., U.S.A. and are described in U.S. Pat. No. 6,156,424 issued on 5 Dec. 2000 in the name of Taylor.

Figure 10:
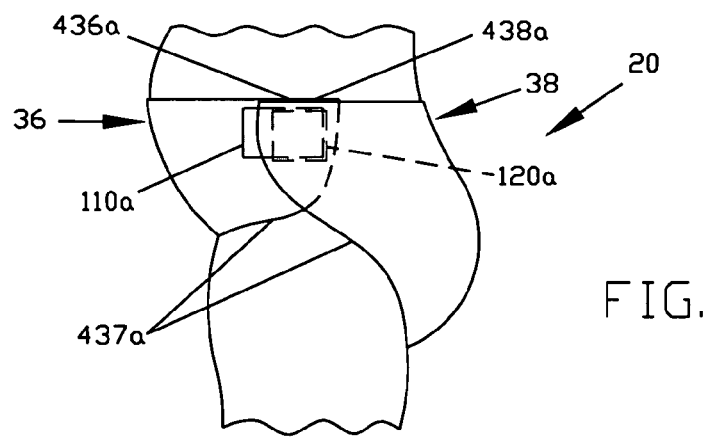
FIG. 10 and FIG. 11 are simplified left and right side elevation views of an exemplary diaper 20 including cohesive fastening patches being worn about a lower torso of a wearer.
Figure 11:
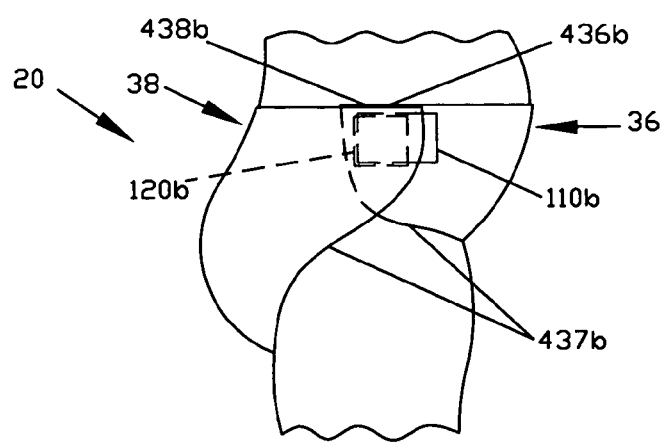

Such cohesive fastening patches may be disposed on the exterior of the diaper 20. For example, as shown in FIG. 1, FIG. 2, FIG. 3, FIG. 5, FIG. 10, and FIG. 11, cohesive fastening patches 110 may be disposed on the exterior surfaces of the respective barrier cuff strips 400 and/or the absorbent assembly 200 in the front waist region 36. In this exemplary embodiment, functionally complementary cohesive fastening patches 120 are disposed on the interior surfaces of the respective barrier cuff strips 400 in the back waist region 38. When the diaper 20 is worn as shown in FIG. 10 and FIG. 11, the cohesive fastening patches on the interior overlap the cohesive fastening patches on the exterior and the cohesion of the overlapped cohesive fastening patches fastens the front waist region 36 and the back waist region 38 together at the sides of the diaper 20. The configuration shown in these figures is adapted for back-over-front fastening.

Alternatively, the front cohesive fastening patches may be disposed on the interior of the diaper 20 and the back cohesive fastening patches may be disposed on the exterior of the diaper 20 in order to adapt the configuration for front-over-back fastening. Alternatively, the cohesive fastening patches may be disposed in a reversible configuration that is adapted to provide the user of the diaper with both options for fastening, i.e., either back-over-front or front-over-back, according to personal preference. For example, cohesive fastening patches that are disposed on both the exterior and the interior of the diaper 20 may allow a back cohesive fastening patch to overlap a front cohesive fastening patch or the front cohesive fastening patch to overlap the back cohesive fastening patch. When the underlying portion of the diaper is extensible, it is preferable that the cohesive fastening patches be similarly extensible such that the underlying extensible portion of the diaper is not restrained.

Figure 14:
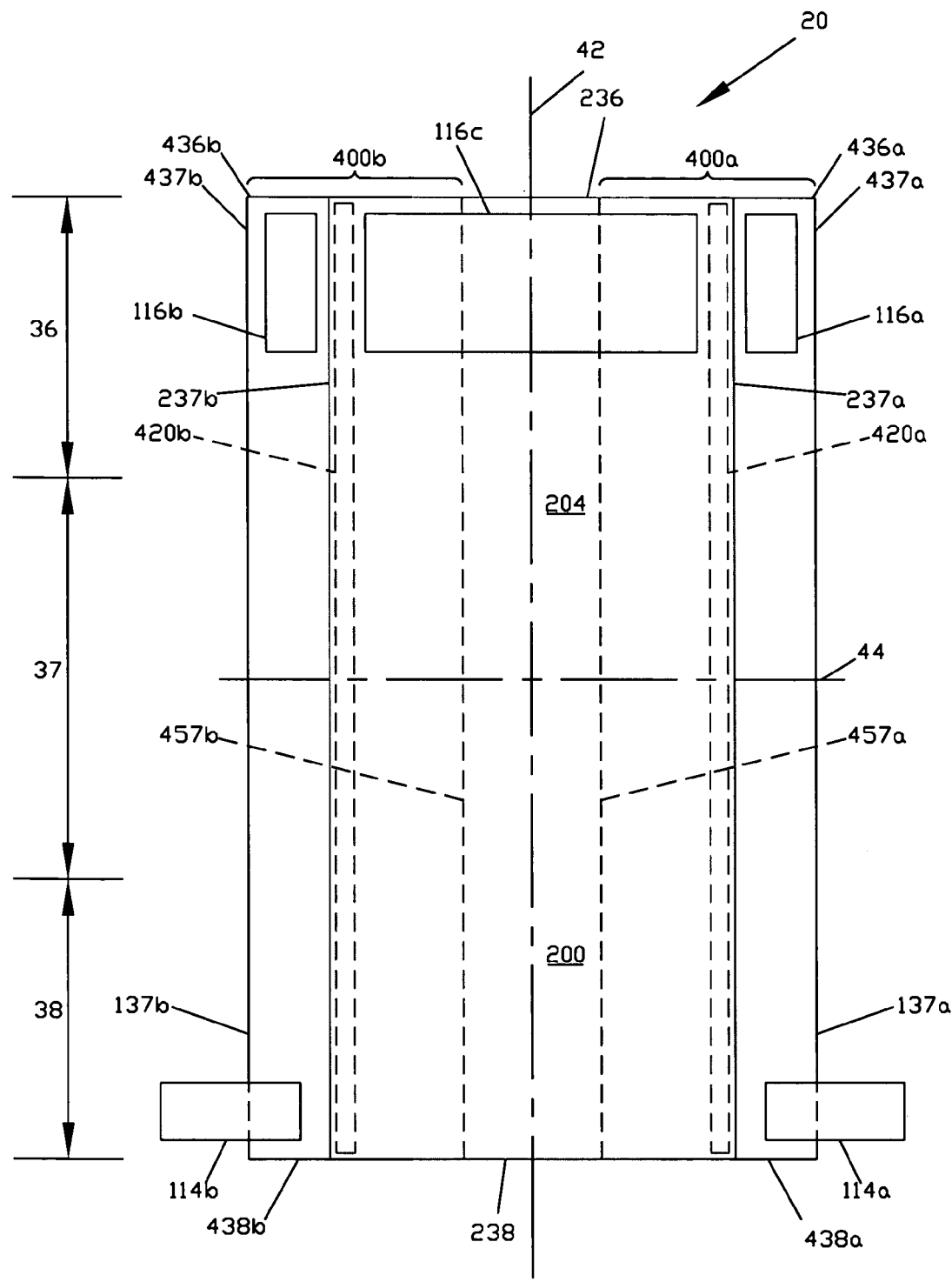
FIG. 14 is a simplified plan view of an exemplary diaper 20, shown in its flat, uncontracted state, i.e., without the contraction induced by elastic members, having adhesive tape tabs 114 and fastening surfaces 116, and with the exterior portion of the diaper 20 that faces outwardly away from the wearer facing the viewer.

Alternatively, adhesive tape tabs may be attached to the diaper 20 and may be used to fasten the back waist region 38 and the front waist region 36 together. For example, as shown in FIG. 14, adhesive tape tabs 114 may be attached to the barrier cuff strips 400 at or adjacent to their distal edges 437. Suitable adhesive tapes are available from the 3M Corporation of St. Paul, Minn., U.S.A., under the designation of XMF99121, and from the Avery Dennison Corporation, Specialty Tape Division, Mentor, Ohio, U.S.A., under the designation of F4416.

Optionally, one or more fastening sheets may also be attached to the diaper 20 and used in conjunction with such adhesive tape tabs. For example, fastening sheets 116 may be attached onto the exterior surfaces 404 of the respective barrier cuff strips 400 and the exterior surface 204 of the absorbent assembly 200 as shown in FIG. 14. When a fastening sheet is provided, the adhesive tape tabs may be adhered to the fastening sheet to fasten the back waist region 38 and the front waist region 36 together. The fastening sheet serves to distribute the tensile force transmitted by each of the adhesive tape tabs over an area larger than the adhered area of the adhesive tape tab and may, itself, bear a portion of the tensile force and thereby relieve a portion of the force exerted on the underlying portion of the diaper, such as the barrier cuff strips. Thus, for example, the incorporation of such a fastening sheet may make it possible to use a relatively inexpensive and relatively weak material for the underlying portion of the diaper. When mechanical fasteners are used instead of adhesive tape tabs, a fastening sheet can have a surface and/or elements that engage with the mechanical fastener, e.g., loops with which hooks may engage. When the underlying portion of the diaper is extensible, it is preferable that the fastening sheet be similarly extensible such that the underlying extensible portion of the diaper is not restrained.

Description of the Absorbent Assembly

In the exemplary diaper 20 shown in FIG. 1, the absorbent assembly 200 extends the full length of the barrier cuff strips 400 between the front waist edges 436 and the back waist edges 438. Such a full length configuration may be desirable in order to minimize the amount of waste material and the difficulty associated with the manufacture of the diaper 20, especially when the method used to manufacture the diaper 20 requires the introduction of the material or materials for the absorbent assembly 200 in the form of a continuous web or multiple continuous webs. Alternatively, the absorbent assembly 200 may be shorter and extend less than the full length of the barrier cuff strips. Such a shorter configuration may be desirable in order to minimize the total amount of material used and the cost of the diaper 20.

Figure 16:
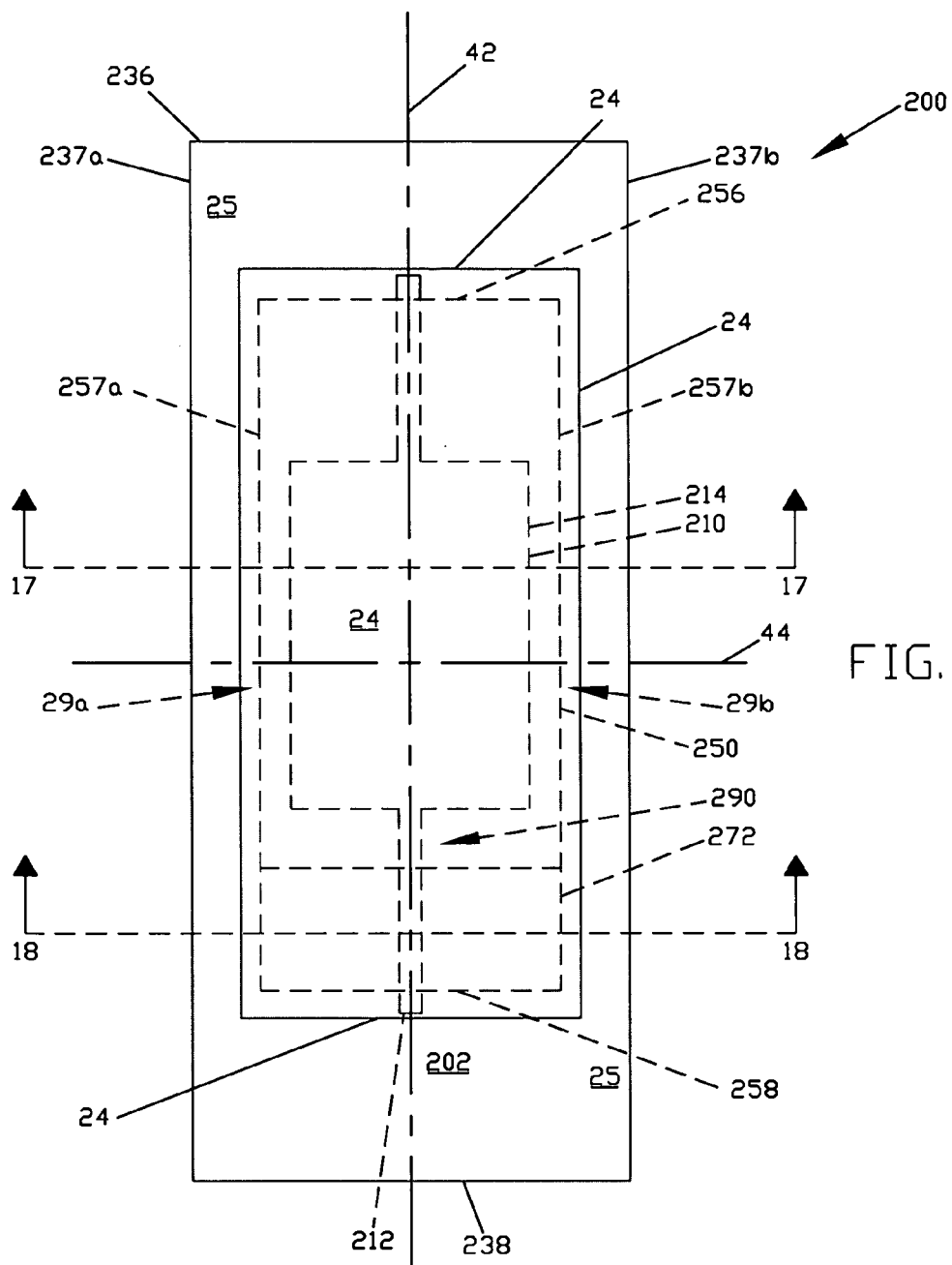
FIG. 16 is a plan view of an exemplary absorbent assembly 200, shown separately from the other portions of an exemplary diaper 20 and with the interior portion of the absorbent assembly 200 that faces inwardly toward the wearer and contacts the wearer facing the viewer.
Figure 17:
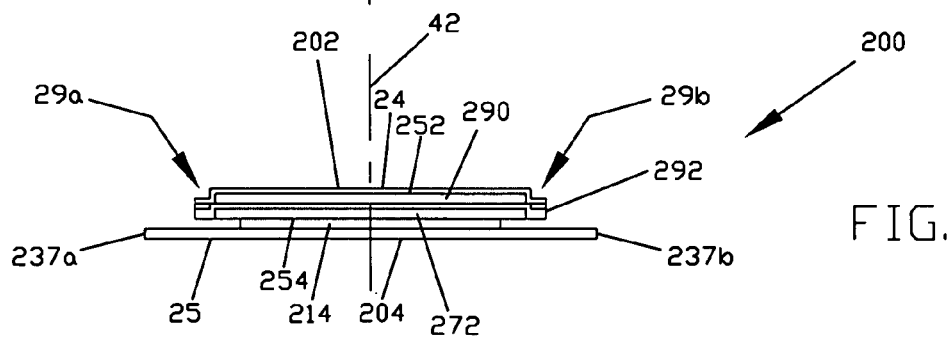
FIG. 17 and FIG. 18 are section views of the absorbent assembly 200 of FIG. 16 taken at the section lines 17-17 and 18-18.
Figure 18:
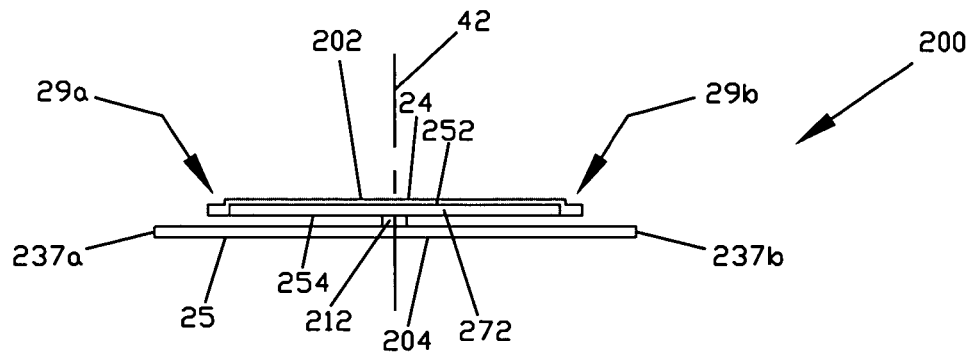

As shown in FIG. 16, FIG. 17, and FIG. 18, the absorbent assembly 200 includes an absorbent core 250 that serves to absorb and retain liquid bodily waste materials. The absorbent core 250 has a front edge 256, a back edge 258, side edgs 257, an interior surface 252, and an exterior surface 254.

The absorbent assembly 200 may include an upper covering sheet that is disposed in a face-to-face arrangement with the interior surface 252 of the absorbent core 250 in addition to a lower covering sheet that is disposed in a face-to-face arrangement with the exterior surface 254 of the absorbent core 250. If both are present, such an upper covering sheet and lower covering sheet may be attached together to contain the absorbent core 250 between them and thereby form the absorbent assembly 200. For example, in the exemplary absorbent assembly 200 shown in FIG. 16, FIG. 17, and FIG. 18, an upper covering sheet 24 and a lower covering sheet 25 are attached together adjacent to the side edges 237 in attachment zones 29a and 29b.

The upper covering sheet is water-permeable and allows liquid bodily waste to pass through its thickness to the absorbent core. The upper covering sheet preferably is formed of a soft material that will not irritate the skin of the wearer, for example a synthetic nonwoven such as spunbonded or carded polyethylene, polypropylene, polyester, or rayon. A portion or the whole of either or both of the upper covering sheet and the lower covering sheet may be water vapor-permeable, i.e., breathable.

The lower covering sheet may include a water-impermeable layer that is formed of a suitable material, for example a film of polyethylene or another polyolefin, a microporous breathable film, a hydrophobic nonwoven, or a film formed of coextruded layers of polypropylene-polyethylene-polypropylene. For example, a suitable coextruded film is available from Clopay Plastic Products Co. of Mason, Ohio, U.S.A. under the designation of M18-327. A multi-layer lower covering sheet, such as a laminate of a film and a nonwoven, may also be suitable and may be oriented with the nonwoven disposed exteriorly to provide the feel and appearance of a cloth-like outermost layer, with the nonwoven disposed interiorly to separate the film from the skin of the wearer, or with nonwovens disposed both exteriorly and interiorly.

The upper covering sheet and the lower covering sheet may extend to the same width and the same length. Alternatively, one or more of the edges of one of the covering sheets may lie distally relative to the respective edge or edges of the other covering sheet. For example, the upper covering sheet may extend longitudinally only to an extent sufficient to cover the absorbent core and to be attached to the lower covering sheet adjacent to either the front or the back edge of the absorbent core, while the lower covering sheet may extend longitudinally beyond the upper covering sheet toward or to the adjacent waist edges of the barrier cuff strips. Similarly, the upper covering sheet may extend laterally only to an extent sufficient to cover the absorbent core and to be attached to the lower covering sheet adjacent to either the left or the right side edge of the absorbent core and the lower covering sheet may extend laterally beyond the upper covering sheet. For example, in the exemplary absorbent assembly 200 shown in FIG. 4, the upper covering sheet 24 extends laterally only a relatively small distance beyond the side edges 257 of the absorbent core 250 and is attached to the lower covering sheet 25 in this area. The lower covering sheet 25 in this exemplary absorbent assembly extends laterally beyond the upper covering sheet 24 and is attached to the barrier cuff strips 400.

The absorbent assembly and the barrier cuff strips may be attached together over any part or the whole of the length of the absorbent assembly. Preferably, the absorbent assembly is attached on its interior surface to the barrier cuff strips in laterally opposing longitudinally extending attachment zones such as the exemplary attachment zones 420a and 420b shown in FIG. 2, FIG. 3, FIG. 4, FIG. 5, and FIG. 14. The portions of the barrier cuff strips that lie outside such an attachment pattern are not restrained by attachment to the absorbent assembly and therefore remain extensible. For example, a relatively narrow longitudinally extending attachment zone such as left attachment zone 420a leaves the majority of the width of the left barrier cuff strip 400a freely extensible and thereby allows extension of the left barrier cuff strip 400a in the lateral direction.

Within the extent of the attachment zones, the absorbent assembly may be attached to the barrier cuff strips continuously or intermittently. For example, a film of an adhesive may be applied continuously over the entire area of the attachment zones and then used to continuously attach the absorbent assembly to the barrier cuff strips. As an alternative example, an adhesive may be applied discontinuously at and inside the boundaries of the attachment zones, such as in the form of dots, stripes, beads, spirals, etc., and then used to attach the absorbent assembly and the barrier cuff strips together.

In some embodiments, one or both of the longitudinally extending attachment zones 420 may act as a dam that prevents the lateral flow of liquid bodily waste in a direction away from the absorbent core toward the adjacent side edge 137 of the diaper. For example, in an embodiment in which the lower covering sheet 25 extends laterally beyond the upper covering sheet 24, as in the exemplary embodiment of FIG. 4, and in which both the lower covering sheet 25 and each of the barrier cuff strips 400 includes a water-impermeable layer, as described above, such a longitudinally extending attachment zone acting as a dam may effectively trap liquid bodily waste materials between the lower covering sheet, the barrier cuff strips, and the body of the wearer of the diaper.

The absorbent core may be attached to the lower covering sheet over any part or the whole of the area of the absorbent core. Preferably, the absorbent core is attached on its exterior surface to the lower covering sheet in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence, or may include detached portions and thereby lack contiguity but still be arranged such that the shape of the overall pattern is a cruciform. An exemplary contiguous cruciform attachment pattern 210 is shown in FIG. 16, FIG. 17, and FIG. 18. When an adhesive is used for the attachment, less may be necessary in a cruciform attachment pattern than in a more extensive attachment pattern. In addition, the portions of the lower covering sheet that lie outside such a cruciform attachment pattern are not restrained by attachment to the absorbent core and therefore remain extensible. In particular, a relatively narrow longitudinally extending portion 212 of a cruciform attachment pattern 210 like that shown in FIG. 16 and FIG. 18 leaves the majority of the width of the lower covering sheet 25 in the front waist region 36 and in the back waist region 38 freely extensible and thereby allows extension of the lower covering sheet 25 in the lateral direction in these regions. A relatively wide laterally extending portion 214 of a cruciform attachment pattern 210 like that shown in FIG. 16 and FIG. 17 prevents the portion of the lower covering sheet 25 in the crotch region 37 to which the absorbent core 250 is attached from shifting relative to the absorbent core 250 in that region.

Within the extent of the cruciform attachment pattern, the absorbent core may be attached to the lower covering sheet continuously or intermittently. For example, a film of an adhesive may be applied continuously over the entire area of the cruciform attachment pattern and then used to continuously attach the absorbent core to the lower covering sheet. As an alternative example, an adhesive may be applied discontinuously at and inside the boundaries of the cruciform attachment pattern, such as in the form of dots, stripes, beads, spirals, etc., and then used to attach the absorbent core to the lower covering sheet. Suitable configurations of cruciform attachment patterns are disclosed in U.S. patent application Ser. No. 10/880,128 filed on 29 Jun. 2004.

The absorbent core 250 includes a storage component 272 that serves to absorb and retain liquid bodily waste materials. Suitable known materials for the absorbent core storage component include cellulose fibers in the form of comminuted wood pulp, which is commonly known as "airfelt", layers or sheets of a natural or synthetic fibrous material or materials, a superabsorbent polymer or polymers, etc. These absorbent materials may be used separately or in combination. Many known absorbent materials may be used in a discrete form, i.e., in the form of fibers, granules, particles, and the like.

Such a discrete form of an absorbent material may be immobilized by an adhesive that attaches the discrete pieces together to form a coherent layer or that attaches the discrete pieces to a substrate layer or that attaches the discrete pieces both to each other and to the substrate layer.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Such an absorbent core acquisition component 290 is shown overlying the absorbent core storage component 272 in FIG. 16, FIG. 17, and FIG. 18. A separation sheet 292 of, e.g., a tissue or a nonwoven material, may be disposed between the absorbent core storage component 272 and the absorbent core acquisition component 290 to help ensure that none of the gel formed by a superabsorbent polymer reaches the skin of the wearer. This separation sheet 292 may extend laterally beyond the side edges 257 of the absorbent core 250 and the upper covering sheet 24 may be attached to the separation sheet 292. In this arrangement, the liquid bodily waste material that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

Figure 19:
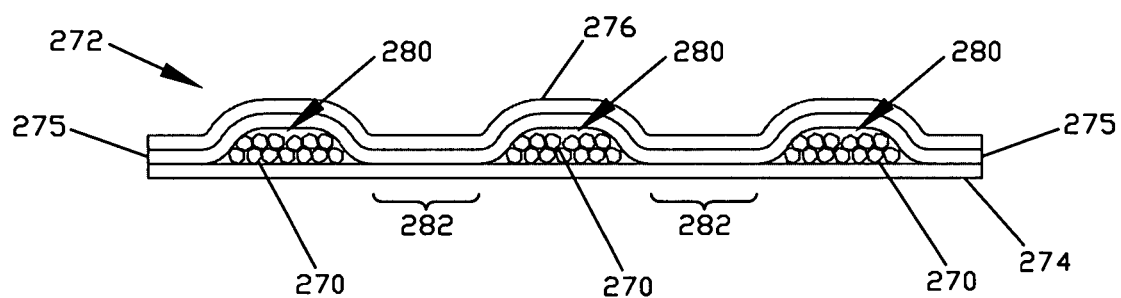
FIG. 19 is a section view of an exemplary absorbent assembly 200 showing details of an exemplary absorbent core having particles of superabsorbent material contained inside pockets

As shown in FIG. 19, in some exemplary embodiments, an absorbent core storage component 272 may include the discrete form of an absorbent material that is immobilized in pockets formed by a layer of a thermoplastic material, such as a hot melt adhesive, that intermittently contacts and adheres to a substrate sheet, while diverging away from the substrate sheet at the pockets. Absorbent core components having such structures and being suitable for the storage of liquid bodily wastes are described in co-pending and commonly assigned U.S. Patent Applications Nos. 10/776,839 and 10/776,851, both filed on 11 Feb. 2004 in the name of Ehrnsperger et al. An exemplary absorbent core storage component 272 having such a structure is shown in FIG. 19. In this absorbent core storage component 272, particles 270 of a superabsorbent polymer are contained inside pockets 280 formed by a layer 275 of a thermoplastic material. The absorbent core storage component may include both particles of a superabsorbent polymer and airfelt and both materials may be contained inside the pockets formed by the layer of the thermoplastic material. Alternatively, as shown in FIG. 19, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 19, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid bodily waste may pass to be absorbed by the particles 270 of the superabsorbent polymer.

In FIG. 19, a separate thermoplastic layer covering sheet 276 is shown overlying the layer 275 of the thermoplastic material. Alternatively, the separate thermoplastic layer covering sheet 276 may be omitted. As another alternative, two absorbent core storage components each like that shown in FIG. 19 except for the omission of the thermoplastic layer covering sheet 276 may be superposed with one absorbent core storage component inverted such that the respective substrate sheets distally oppose each other. In such a combination of absorbent core storage components, either or both of the distally opposing substrate sheets may serve respectively as either or both of an upper covering sheet and a lower covering sheet for the absorbent assembly. Alternatively, the absorbent assembly may include a separate lower covering sheet and/or a separate upper covering sheet.

Figure 20:
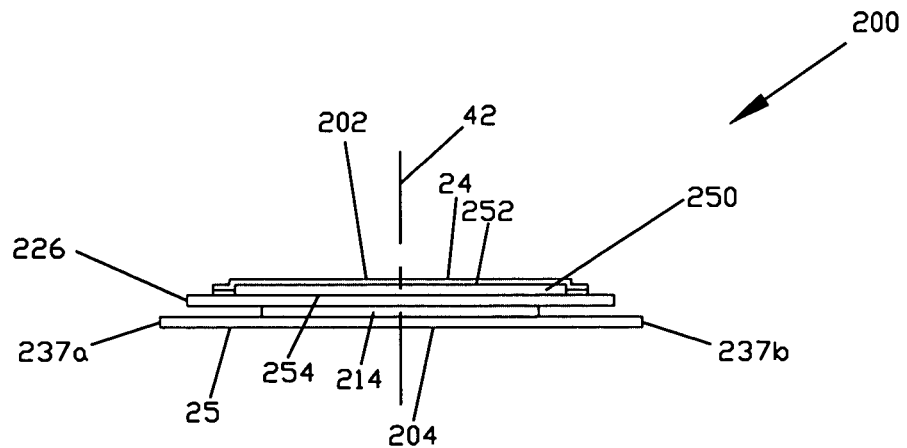
FIG. 20 is a section view of an exemplary absorbent assembly 200 having an additional bottom sheet 226, taken at a section line corresponding to the section line 4-4 in FIG. 1.

The absorbent assembly may include an additional bottom sheet of a film or other water-impermeable material to enhance the protection against leakage. For example, as shown in FIG. 20, an additional bottom sheet 226 of a film or other water-impermeable material may be attached inside the absorbent assembly between the lower covering sheet 25 and the absorbent core 250. Alternatively, the additional bottom sheet may be attached to the absorbent assembly exteriorly of the lower covering sheet. This additional bottom sheet may extend laterally less far than either or both of the side edges 237 of the absorbent assembly 200, as shown in FIG. 20, or may extend laterally to overlap one or both of the side edges of the absorbent assembly.

When such an additional bottom sheet is attached inside the absorbent assembly between the lower covering sheet and the absorbent core, the additional bottom sheet may be attached to the lower covering sheet in a cruciform attachment pattern similar to that shown in FIG. 16, thus leaving the portions of the lower covering sheet that lie outside the cruciform attachment pattern unrestrained by attachment to the additional bottom sheet and allowing these portions to be extensible. For example, a laterally extending portion 214 of such a cruciform attachment pattern is shown in FIG. 20.

Alternatively or in addition, the additional bottom sheet in such an embodiment may be attached in such a cruciform attachment pattern to the absorbent core, thus leaving the portions of the additional bottom sheet that lie outside the cruciform attachment pattern unrestrained by attachment to the absorbent core and therefore allowing these portions to be extensible. In such an embodiment, even if the additional bottom sheet is attached to the lower covering sheet in a pattern other than a cruciform, the lower covering sheet is not indirectly restrained by the absorbent core and therefore is allowed to be extensible.

Description of Shape of Article

Figure 2:
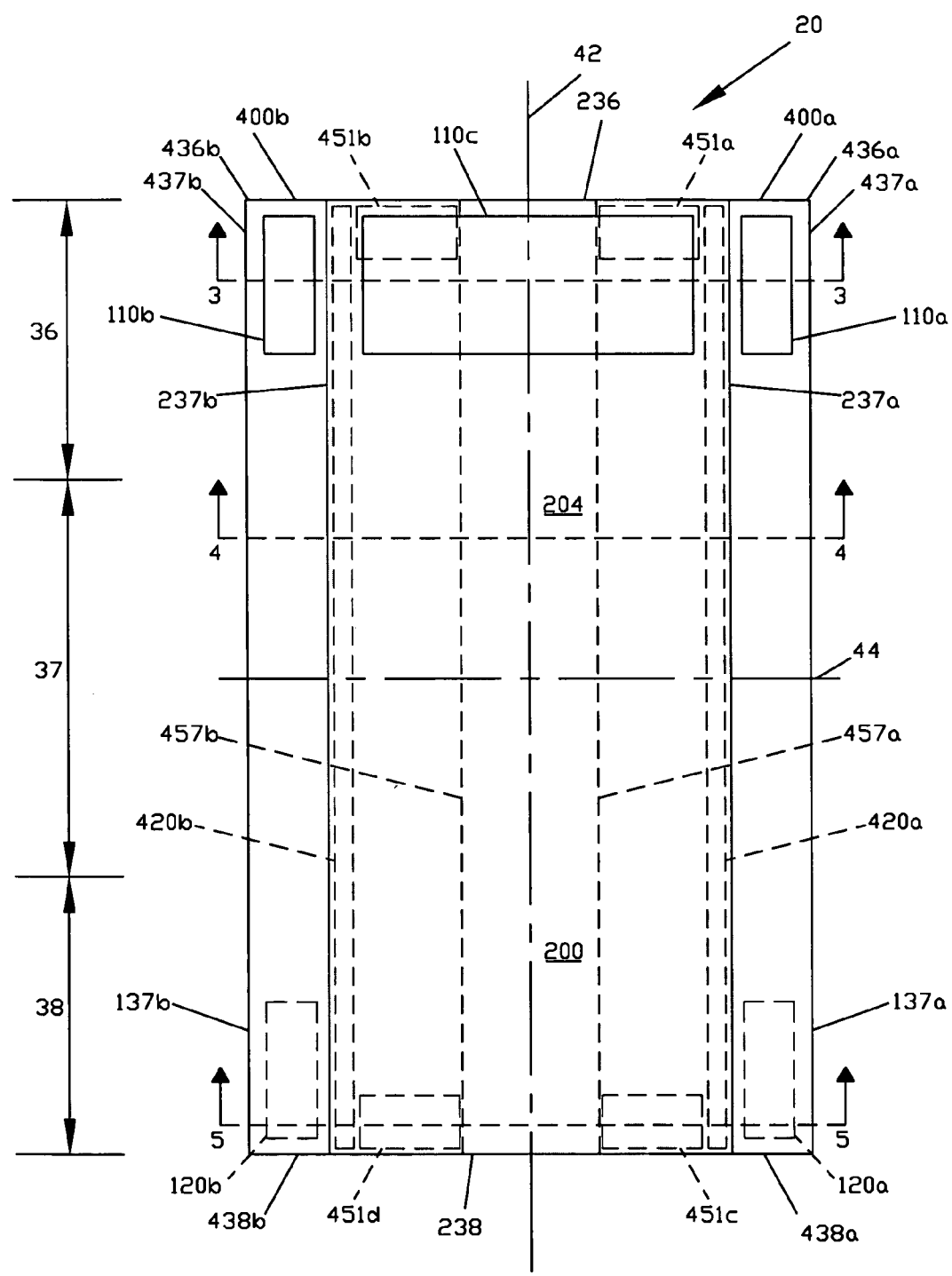
FIG. 2 is a plan view of the diaper 20 of FIG. 1 with the exterior portion of the diaper 20 that faces outwardly away from the wearer shown facing the viewer.

The finished diaper may have a generally rectangular shape, as in the exemplary diaper 20 shown in FIG. 1 and FIG. 2. Such a generally rectangular configuration may be desirable in order to minimize the amount of waste material and the difficulty associated with the manufacture of the diaper 20. Alternatively, the diaper may have side edges 137 that are not straight, but instead are curved and/or notched, thereby giving an overall shape in plan view of an hourglass or of an "I" to the diaper 20. Such a non-rectangular configuration may be desirable in order to impart a tailored appearance to the diaper 20 when it is worn. Such a non-rectangular configuration may also be desirable in order to impart an impression that the diaper 20 will fit comfortably between the legs of a wearer.

Figure 21:
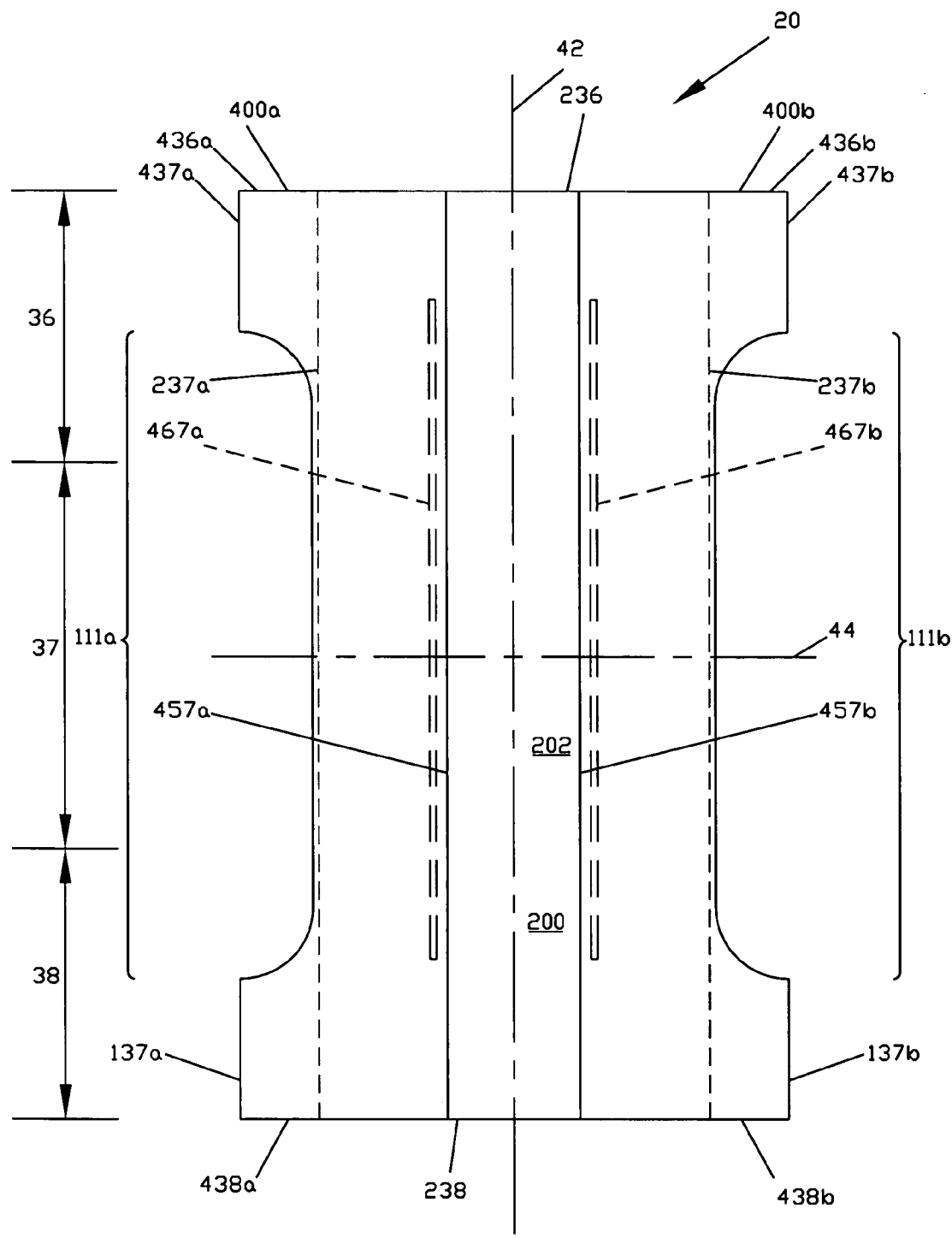
FIG. 21 is a plan view of another exemplary disposable absorbent article in the form of a diaper 20, shown in its flat, uncontracted state and with its interior portion facing the viewer.

Any one of many well-known ways may be used to form a non-rectangular configuration of the diaper. For example, laterally distal portions may be removed from the diaper to make its lateral dimension at and adjacent to the lateral axis 44 smaller than its lateral dimension at and adjacent to the front waist edge 436 and smaller than its lateral dimension at and adjacent to the back waist edge 438, i.e., to make the diaper narrower in the crotch region 37 than at the waist edges. An exemplary form of such a non-rectangular configuration of the diaper is shown in FIG. 21. As shown in this figure, portions of the barrier cuff strips 400 may be removed to form laterally opposing side notches 111a and 111b.

The disclosures of all patents, patent applications and any patents which issue thereon, as well as any corresponding published foreign patent applications, and all publications listed and/or referenced in this description, are hereby incorporated in their entireties herein by reference. It is expressly not admitted that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the following claims are intended to cover all such changes and modifications that are within the scope of this invention.

What is claimed is:

1. A disposable diaper having a front waist region, a back waist region, a crotch region between the waist regions, a longitudinal axis, and a lateral axis, and comprising:
    an absorbent assembly;
    two laterally opposing longitudinally extending barrier cuff strips attached to the absorbent assembly;
    each barrier cuff strip having a longitudinally extending proximal edge and a longitudinally extending elastic gathering member attached adjacent to its proximal edge;
    each barrier cuff strip folded over itself to form an upper layer and a lower layer both formed of a water vapor-permeable nonwoven material, the lower layers being attached to the absorbent assembly in a pair of laterally opposing first attachment zones adjacent to the respective side edges of the absorbent assembly, both the upper layer and the lower layer of each barrier cuff strip extending laterally from the proximal edge at least to the first attachment zone;
    wherein each baffier cuff strip is attached directly to a surface of a lower covering sheet of the absorbent assembly, and wherein at least a portion of a distal edge of the upper layer of each barrier cuff strip extends laterally outward beyond a distal edge of the absorbent assembly underlying each barrier cuff strip.

2. The disposable diaper of claim 1 wherein at least a portion of one of the waist regions is laterally extensible to a greater degree than at least a portion of the crotch region.

3. The disposable diaper of claim 1 wherein at least a portion of the one of the barrier cuff strips laterally outward of the respective first attachment zone is laterally extensible.

4. A disposable diaper having a front waist region, a back waist region, a crotch region between the waist regions, a longitudinal axis, and a lateral axis, and comprising:
    an absorbent assembly including an absorbent core having an exterior surface on which it is attached to a lower covering sheet in a cruciform pattern of attachment having a longitudinally extending portion intersecting with a laterally extending portion;
    two laterally opposing longitudinally extending barrier cuff strips attached to the absorbent assembly;
    each barrier cuff strip having a longitudinally extending proximal edge and a longitudinally extending elastic gathering member attached adjacent to its proximal edge;
    each barrier cuff strip folded over itself to form an upper layer and a lower layer both formed of a water vapor-permeable nonwoven material, the lower layers being attached to the absorbent assembly in a pair of laterally opposing first attachment zones adjacent to the respective side edges of the absorbent assembly, both the upper layer and the lower layer of each barrier cuff strip extending laterally from the proximal edge at least to the first attachment zone; and
    wherein at least a portion of a distal edge of the upper layer of each barrier cuff strip extends laterally outward beyond a distal edge of the absorbent assembly underlying each barrier cuff strip.

5. The disposable diaper of claim 4 wherein the longitudinally extending portion is disposed symmetrically with respect to the longitudinal axis and the laterally extending portion is disposed asymmetrically with respect to the lateral axis.

6. The disposable diaper of claim 5 wherein the laterally extending portion is offset toward the front waist region.

* * * * *

UNITED STATES PATENT AND TRADEMARK OFFICE
CERTIFICATE OF CORRECTION

PATENT NO. : 7,695,463 B2  Page 1 of 1
APPLICATION NO. : 11/158563
DATED : April 13, 2010
INVENTOR(S) : LaVon et al.

It is certified that error appears in the above-identified patent and that said Letters Patent is hereby corrected as shown below:

Column 16

Line 7, delete "baffier" and insert --barrier--.

Signed and Sealed this
Eighth Day of November, 2011

David J. Kappos
*Director of the United States Patent and Trademark Office*